United States Patent
Gridnev et al.

(10) Patent No.: US 6,740,618 B2
(45) Date of Patent: May 25, 2004

(54) ALKYL COBALT(III) DIOXIMATES AND PROCESS FOR FORMING THE SAME

(75) Inventors: Alexei A. Gridnev, Wilmington, DE (US); Gregorii A. Nikiforov, Moscow (RU)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/371,891

(22) Filed: Feb. 21, 2003

(65) Prior Publication Data

US 2003/0135054 A1 Jul. 17, 2003

Related U.S. Application Data

(62) Division of application No. 09/845,865, filed on Apr. 30, 2001, now Pat. No. 6,559,327.
(60) Provisional application No. 60/259,576, filed on Jan. 3, 2001.

(51) Int. Cl.[7] .............................. C07F 9/80; B01J 31/00
(52) U.S. Cl. ..................... 502/152; 502/156; 556/35; 558/87; 558/96
(58) Field of Search ................ 502/152, 156; 556/35; 558/87, 96

(56) References Cited

U.S. PATENT DOCUMENTS

| | | |
|---|---|---|
| 4,526,945 A | 7/1985 | Carlson et al. |
| 4,680,352 A | 7/1987 | Janowicz et al. |
| 4,694,054 A | 9/1987 | Janowicz |
| 5,028,677 A | 7/1991 | Janowicz |
| 5,324,879 A | 6/1994 | Hawthorne |
| 5,362,813 A | 11/1994 | Antonelli et al. |
| 5,412,039 A | 5/1995 | Barsotti et al. |
| 5,587,431 A | 12/1996 | Gridnev et al. |
| 5,773,534 A | 6/1998 | Antonelli et al. |
| 5,847,060 A | 12/1998 | Gridnev et al. |
| 5,928,829 A | 7/1999 | Cheng et al. |

OTHER PUBLICATIONS

Schrauzer et al., Cobalamin Model Compounds. Preparation and Reactions of Substituted Alkyl– and Alkenylcobaloximes and Biochemical Implications, J. of the Amer. Chem. Soc., vol. 89, No. 9, 1967, pp. 1999–2007.

Schrauzer et al., Alkylcobaloximes and their Relation to Alkylcobalamines, J. of the Amer. Chem. Soc., vol. 88, No. 16, 1966, pp 3738–3743.

*Primary Examiner*—Alan L. Rotman
*Assistant Examiner*—Raymond Covington
(74) *Attorney, Agent, or Firm*—Sudhir Deshmukh

(57) ABSTRACT

This invention is directed to alkyl cobalt (III) dioximates and methods for making these dioximates. The alkyl cobalt (III) dioximate has the following structural formula:

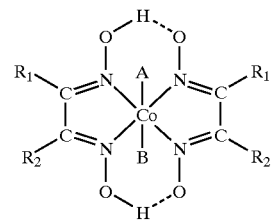

wherein $R_1$, and $R_2$ are individually selected from the following group: H, alkyl having at least 2 carbon atoms, substituted alkyl, aryl, substituted aryl, $COOR_5$, $CONR_6R_7$, $SR_7$, $SO_2R_7$, $SO_2NR_5R_6$, $SOR_5$, $SO_3R_5$, halogen, $CCl_3$, $CF_3$, $COR_5$, CHO, $CR_6R_7OR_5$, $CH(OR_5)(OR_6)$, $CR_5(OR_6)(OR_7)$; where $R_5$, $R_6$, and $R_7$ are independently selected from the following group: H, alkyl, substituted alkyl, aryl or substituted aryl and A is a substituted alkyl derived from an olefinic component and B is a component of a Lewis base and where the substituents of the substituted alkyl are individually selected from the group of ester, ether, amide, halogen, ketone, hydroxy, aryl, $SO_2$-alkyl, sulfamido, and amino groups and the substituents for the substituted aryl are individually selected from the group of ester, ether, amide, halogen, ketone, hydroxy, alkyl, $SO_2$-alkyl, sulfamido, and amino groups.

6 Claims, No Drawings

ALKYL COBALT(III) DIOXIMATES AND PROCESS FOR FORMING THE SAME

CROSS REFERENCE TO RELATED APPLICATION

This application is a divisional of application Ser. No. 09/845,865 filed Apr. 30, 2001 now U.S. Pat. No. 6,559,327 and allowed on Jan. 14, 2003, which, in turn, had a priority from Provisional Application No. 60/259,576, filed Jan. 3, 2001

BACKGROUND OF THE INVENTION

This invention is directed to certain cobalt chelates and to an improved process for forming cobalt chelates and in particular, to alkyl cobalt (III) dioximates and a process that provides an improved yield and purity of such dioximates.

Cobalt chelates have been widely used in the polymerization of high and low molecular weight polymers, and in the formation of oligomers, macromoners, and latices. Also, cobalt (II) chelates have been used as chain transfer agents in free radical polymerizations to form polymers. Acrylic graft copolymers having an acrylic copolymer core and macromonomers grafted thereto have been prepared utilizing cobalt chelates. The synthesis of terminally unsaturated oligomers and functionalized diene oligomers using cobalt chelate catalysts also are known.

G. N. Schrauzer, Wingassen, *J. Am. Chem. Soc.* 89(1967) 1999, shows the formation of an alkyl chelate, i.e., an alkyl cobalt (III) dioximate, using dimethylglyoxime but the yield was low (45%) and purity less than 80%. The method when used with other glyoximes such as diphenylglyoxime, methylcarboxyethylglyoxime and methyldiphenylglyoxime did not form an alkyl cobalt (III) dioximate. There is a need for a process that will produce an alkyl cobalt (III) dioximate in a high yield and in a high purity. The process should allow for the formation of alkyl cobalt (III) dioximates by using glyoximes other than dimethylgloxime since such other glyoximes can impart important properties to the chelate, such as shelf stability and solubility in a variety of solvents. Such properties make the chelate more versatile and useful and cost effective in polymerization processes used for a variety of monomers.

SUMMARY OF THE INVENTION

This invention is directed to alkyl cobalt (III) dioximates and methods for making these dioximates. The alkyl cobalt (III) dioximate has the following structural formula:

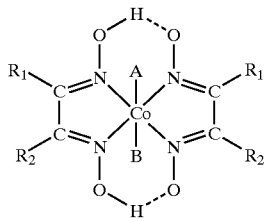

wherein $R_1$, and $R_2$, are individually selected from the following group: H, alkyl having at least 2 carbon atoms, substituted alkyl, aryl, substituted aryl, $COOR_5$, $CONR_6R_7$, $SR_7$, $SO_2R_7$, $SO_2NR_5R_6$, $SOR_5$, $SO_3R_5$, halogen, $CCl_3$, $CF_3$, $COR_5$, CHO, $CR_6R_7OR_5$, $CH(OR_5)(OR_6)$, $CR_5(OR_6)(OR_7)$; where $R_5,R_6$, and $R_7$ are independently selected from the following group: H, alkyl, substituted alkyl, aryl or substituted aryl and A is a substituted alkyl derived from an olefinic component and B is a component of a Lewis Base and where the substituents of the substituted alkyl are individually selected from the group of ester, ether, amide, halogen, ketone, hydroxy, aryl, $SO_2$-alkyl, sulfamido, and amino groups and the substituents for the substituted aryl are individually selected from the group of ester, ether, amide, halogen, ketone, hydroxy, alkyl, $SO_2$-alkyl, sulfamido, and amino groups.

DETAILED DESCRIPTION OF THE INVENTION

The alkyl cobalt (III) dioximate of this invention is formed by a novel process in which a mixture of a cobalt (II) salt, a dioxime, an olefinic component and a Lewis base is treated with molecular hydrogen under pressure of 0.7 to 70 kg/cm². The cobalt (II) salt, dioxime, olefinic component, and the Lewis base are reacted in a molar ratio of 1:2:1:1. Typically, the hydrogen is under a high pressure of 14 to 70 kg/cm², preferably, 18 to 30 kg/cm² unless a Lewis base of an imidazole, phosphine or phosphite is used. If such a Lewis base is used, the hydrogen pressure can be reduced to 0.7 to 14 kg/cm² preferably, 1 to 2 kg/cm². Typical treatment time with hydrogen under pressure is 0.5 to 5.0 hours, preferably 4 to 6 hours. Typical reaction temperatures are –20 to 50° C. and preferably 17 to 30° C.

Particular advantages of the novel process are that the yields are high, i.e., 70% and over and that the purity is high, 80% and over, of the alkyl cobalt (III) dioximate formed.

Typical cobalt (II) salts that can be used are acetates, nitrates, chlorides, bromides, iodides, fluorides, sulfates, fluoroborate, hexafluorophosphate or hexafluoroantimonate either as hydrated or anhydrous, or as an alkanoate. Mixtures of any of the aformentioned cobalt (II) salts also can be used. Lower ($C_2$ to $C_3$) alkanoates are soluble in methanol or propanol and the higher ($C_4$ to $C_8$) alkanoates are soluble in hydrocarbon solvents. Typical examples of the above cobalt salts are cobalt chloride, cobalt chloride hexahydrate, cobalt acetate, cobalt acetate tetrahydrate, cobalt nitrate, cobalt bromide, cobalt iodide, cobalt difluoride, cobalt ammonium sulfate and cobalt 2-ethylhexanoate. Preferred are cobalt chloride hexahydrate and cobalt acetate tetrahydrate Typical dioximes that can be used have the structural formula $R_1$—C(=NOH)—C(=NOH)—$R_2$ where $R_1$ and $R_2$ are described above. Typical dioximes are as follows: diphenylglyoxime, carboxyethylmethylglyoxime, methyl phenylglyoxime, dimethylamidolcarbonylmethylglyoxime, 4-amidophenylamidylcarbonylmethylglyoxime, trifluoroacetyl-triflouromethyglyime, camphordiquinonedioxime, 1,2-cyclohexanedioxime, furildioxime, thiophenylglyoxime, and di(butylthio) glyoxime. Preferred are diphenylglyoxime and carboxyethylmethylglyoxime.

A Lewis base is used in the process to form the cobalt (III) dioximate of this invention and forms the A component of the dioximate. It is believed that the Lewis base activates the cobalt in the reaction with hydrogen and forms a coordination bond with the cobalt. Typically useful Lewis bases are alcohols, such as methanol, ethanol, propanol, isopropanol, n-butanol, isobutanol, water (under some conditions); alkyl mercaptanes, such as ethyl mercaptane, thiophenole, dodecyl mercaptan; amines, such as pyridine, 4-methylpyridine, nicotineamide, 2-methyl pyridine, and 4-dimthylaminopyridine. Pyridine is preferred.

When imidazoles, phosphines or phosphites are used as the Lewis Base constituent, the pressure of molecular hydrogen can be lowered significantly as stated above. It is believed that when these three aforementioned compounds are used, they activate the cobalt in the reaction with hydrogen to a greater extent and hydrogen under a lower pressure, such as 0.7–14 kg/cm$^2$, can be used. Typically useful imidazoles have the structural formula:

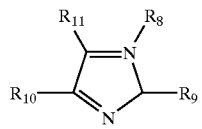

wherein $R_8$, $R_9$, $R_{10}$, and $R_{11}$ are each selected from the following: H, alkyl, aryl, $NR_5,N_6$, $SR_7$, $SO_2R_7$, $SO_2NR_5R_6$, $SOR_5$, $COR_5$, CHO, $CR_6R_7OR_5$, $CH(OR_5)(OR_6)$, and $CR_5(OR6)(OR_7)$; and where $R_5$, $R_6$, and $R_7$ are each selected from the following group: H, alkyl and aryl.
Examples of such imidazoles are as follows: unsubstituted imidazole, 2-methyl imidazole, 2-phenyl imidazole, 1,2 dimethyl imidazole, 1,2 diethyl imidazole, 1-methyl-2-ethyl imidazole, 1-butyl imidazole, and 2,5-dimethyl-4-hydroxymethyl imidazole. 1,2 Dimethyl imidazole and 1-butyl imidazole are preferred.

Phosphines that can be used have the formula $P(R_{14})(R_{15})(R_{16})$, wherein $R_{14}$, $R_{15}$, $R_{16}$ are each selected from the following group: H, alkyl and aryl. Typically useful phosphines used are triphenyl phosphine and triethyl phosphine. Phosphites that can be used have the formula $P(OR_{17})(OR_{18})(OR_{19})$, where $R_{17}$, $R_{18}$, and $R_{19}$ are each selected from the following group: H, alkyl and aryl. Typically useful phosphites are triethylphosphite, triphenylphosphite, and tricresylphosphite.

The olefinic component included in the B component of the alkyl cobalt (III) dioximate forms a coordination bond with the cobalt constituent of the dioximate. Typically olefinic compounds that are used in the process of this invention are alkyl acrylates, i.e., alkyl esters of acrylic acid, such as methyl acrylate, ethyl acrylate, propyl acrylate, methoxy ethyl acrylate, phenoxy ethyl acrylate, isopropyl acrylate, butyl acrylate, pentyl acrylate, and ethylhexyl acrylate. Methyl acrylate is preferred.

Other olefinic components that can be suitably used such as styrene, methyl styrene, acrylonitrile, acrylamide, dimethylolacrylamide, vinyl pyrrolidone, vinyl chloride, vinyl acetate, maleic anhydride, N-methylmaleimide, and other vinylic monomers of the following structure:

where X is an amide, imide, ester, aryl, halogen, pseudo halogen (thiocyanates), isocyanate, nitrile, ether, carbamyl, substituted amine and thio ether.

Suitable solvents that can be used in the process are alcohols, such as methanol, ethanol, propanol, isopropanol, butanol, isobutanol, and any mixtures thereof. Other common organic solvents that can be used are diethyl ether, ethylene glycol, polyethylene glycol monoalkyl and dialkyl ethers, propylene carbonate, N-methyl pyrrolidone, amides, dimethylsulfoxide, and Cellosolves® and Carbitols® both supplied by supplied by Union Carbide Corp. Danbury, Conn. Water and mixtures of water and the aforementioned solvents can be used.

The novel process of this invention provides for high purity alkyl cobalt (III) dioximate and in a high yield. Yields are 70% and over and preferably 75% and up to 100% and purity is over 80% and preferably over 85% up to 100%.

In one preferred alkyl cobalt (III) dioximate, $R_1$ and $R_2$ are phenyl, A is (methoxycarbonyl) ethyl and B is pyridine; in another preferred alkyl cobalt (III) dioximate, $R_1$ and $R_2$ are phenyl, A is (methoxycarbonyl) ethyl and B is dimethyl imidazole; in still another preferred alkyl cobalt (III) dioximate, $R_1$ and $R_2$ are phenyl, A is (methoxycarbonyl) ethyl and B is triphenylphosphine. The alkyl cobalt (III) dioximate is an excellent chain transfer agents used in free radical polymerization of polymers, macromonomers, oligomers, low molecular weight polymers (Mw 200 to 1,000), medium molecular weight polymers (Mw 1,000 to 50,000) and high molecular weight polymer (Mw 500,000 and over), latex polymers, graft copolymers, star polymers, hyperbranched polymers, core shell structured polymers and other polymer compositions.

The following examples illustrate the invention. All parts and percentages are on a weight basis unless otherwise indicated.

EXAMPLES

Example 1

This example was directed to the synthesis of an alkyl cobalt (III) dioximate under a high pressure of molecular hydrogen (21 kg/cm$^2$).

The following constituents were charged into a pressure vessel equipped with a stirrer and stirred for a 5 hour period under hydrogen gas at a pressure of 21 kg/cm$^2$ and a temperature of 25° C.: 48 g of diphenylglyoxime (0.2 moles), 25 g of cobalt acetate tetrahydrate, 8.6 g of methyl acrylate (0.1 mol), 8 ml of pyridine (0.1 mol) and 500 ml methanol. The resulting reaction mixture was filtered and organic crystals of a cobalt (III) complex were obtained. The resulting cobalt (III) complex was identified by NMR (nuclear magnetic resonance) as an alkyl cobalt (III) dioximate that had the formula as shown in the above specification wherein $R_1$ and $R_2$ were phenyl, A was 1-(methoxycarbonyl)ethyl and B was pyridine. The yield was 54 g (70%) and the purity measured by (NMR) was 90–95%.

A polymethylmethacrylate polymer was prepared using the above alkyl cobalt (III) dioximate. The following constituents were charged into a reaction vessel equipped with a stirrer, nitrogen inlet and a heating mantle: 30 ml methyl methacrylate monomer (MMA), 60 mg azobisisobutyronitrile, and 6 mg of the above prepared alkyl cobalt (III) dioximate. The resulting reaction mixture was under a blanket of nitrogen and held at 75° C. for 3 hours. A polymethylmethacrylate polymer was formed having a Mn=334 (Number Average Molecular Weight) determined by GPC (gel permeation chromatography).

A comparative polymethylmethacrylate polymer was prepared using the same constituents and similar proceedure set forth above except the alkyl cobalt (III) dioximate was omitted. The polymethylmethacrylate polymer that was formed had a Mn=72,000 determined by GPC. Thus, it can be seen that the addition of alkyl cobalt (III) dioximate resulted in controlling the molecular weight of the polymer being formed.

Example 2

This example was directed to the synthesis of an alkyl cobalt (III) dioximate using very high pressure hydrogen (70 kg/cm$^2$). The synthesis followed the procedure of Example 1 using the same constituents except the pressure of hydrogen was increased to 70 kg/cm$^2$. The resulting product was identical to the alkyl cobalt (III) dioximate of Example 1 (determined by NMR). The yield was 83% and the purity >95%. Thus, it can be seen that due to the use of higher pressure of hydrogen, the yield increased by 13% and there was a slight increase in purity in comparison to Example 1 in which lower pressure hydrogen was used.

Example 3 Comparative Example

This example was directed to a synthesis using low pressure hydrogen (10.5 kg/cm$^2$) in an attempt to form an alkyl cobalt (III) dioximate. The synthesis followed the procedure of Example 1 using the same constituents except the pressure of hydrogen was decreased to 10.5 kg/cm$^2$. The product formed was predominately a Co(II) complex as determined by NMR. Thus, it can be seen that when the process was run under low pressure hydrogen (10.5 kg/cm$^2$), an alkyl cobalt (III) dioximate was not formed.

Example 4 Comparative Example

This comparative example was directed to the synthesis of G. N. Schrauzer, R. J. Windgassen, J. Am. Soc. 89 (1967) 1999 that did not disclose the use of molecular hydrogen under pressure to form the cobalt complex.

A mixture of 46.6 g of dimethylglyoxime (0.4 mol), 47.6 g of cobalt chloride tetrahydrate (0.2 mol) were dissolved in 800 ml of methanol. Then 16.4 g of sodium hydroxide (0.4 mole) in 100 ml of water were added with 16 ml of pyridine (0.2 mol). After 15 minutes, 0.2 mol of methyl acrylate was added and then molecular hydrogen was bubbled through the resulting reaction mixture. After 0.1 mol of hydrogen was absorbed, the reaction mixture was filtered. Crystals of alkyl cobalt (III) dioximate determined by NMR were obtained and washed with methanol and dried in a vacuum. Yield was 45% and the purity was >80%.

This process is only operative when dimethylglyoxime is used as shown in the following comparative examples 5–7.

Example 5 Comparative Example

This synthesis was directed to the procedure of Example 4 except methyl carboxyethylglyoxime was used instead of dimethylglyoxime. No alkyl cobalt (III) dioximate was formed.

Example 6 Comparative Example

This synthesis was directed to the procedure of Example 4 except methyl diphenylglyoxime was used instead of dimethylglyoxime. No alkyl cobalt (III) dioximate was formed.

Comparative Examples 5 and 6 show that when glyoximes other than dimethylglyoxime were used, an alkyl cobalt (III) dioximate was not formed using the process of Schrauzer et al (Example 4).

Example 7 Comparative Example

This example was directed to a synthesis that used water instead of pyridine and used hydrogen under very high pressure (140 kg/cm$^2$) in an attempt to form an alkyl cobalt (III) dioximate. The synthesis followed the procedure of Example 1 using the same constituents except water was used instead of pyridine and the pressure of hydrogen was increased to 140 kg/cm$^2$. No crystalline product was formed. This example showed that a Lewis base, such a pyridine, was needed to form the alkyl cobalt (III) dioximate of this invention.

Example 8

This example was directed to a synthesis that used an imidazole in place of pyridine and hydrogen was used under low pressure. The synthesis followed the procedure of Example 1 using the same constituents except 1,2 dimethyl imidazole was used instead of pyridine and the pressure of hydrogen was decreased to 10.5 kg/cm$^2$. The resulting reaction mixture was filtered and organic crystals of an alkyl cobalt (III) dioximate identified by NMR were obtained. The resulting alkyl cobalt (III) dioximate had the formula as shown in the above specification wherein $R_1$ and $R_2$ were phenyl, A was 1-(methoxycarbonyl)ethyl and B was 1,2 dimethyl imidazole. The yield was (70%) and the purity as measured by NMR was 90%.

Example 9

This example was directed to a synthesis that used a phosphine in place of pyridine and hydrogen under low pressure. The synthesis followed the procedure of Example 1 using the same constituents except triphenylphosphine was used instead of pyridine and the pressure of hydrogen was decreased to 2.1 kg/cm$^2$. The resulting reaction mixture was filtered and organic crystals of a cobalt (III) complex were obtained. The cobalt (III) complex was identified by NMR as an alkyl cobalt (III) dioximate. The resulting alkyl cobalt (III) dioximate had the formula as shown in the above specification wherein $R_1$ and $R_2$ were phenyl, A was 1-(methoxycarbonyl)ethyl and B was triphenylphosphine. The yield was (72%) and the purity as measured by NMR was 80%.

Example 10 Comparative Example

This example was directed to a synthesis that used hydrogen under ultra low pressure. A mixture of 9.3 g of dimethylglyoxime (0.08), 10 g of cobalt acetate tetrahydrate (0.04 mol), 3.6 g methyl acrylate (0.04 mol), 5.3 ml of n-butyl imidazole (0.1 mol) and 150 ml methanol were stirred under a pressure of 0.007 kg/cm$^2$ of hydrogen in $CO_2$ for 6 hours. The resulting reaction mixture was diluted with 40 ml water and orange crystals were filtered off and identified by NMR as the alkyl cobalt (III) dioximate of this invention where A was 1-(methoxycarbonyl) ethyl and B was n-butyl imidazole. The yield was 6 g (30%) and purity as measured by NMR was 80%.

Example 10 showed that under low hydrogen pressure using an imidazole, the alkyl cobalt (III) dioximate of this invention was formed. The yield was unacceptable for a viable commercial process.

Example 11 Comparative Example

This example was directed to a synthesis that used hydrogen under ultra low pressure and used pyridine instead of an imidazole of Example 10. The synthesis followed the procedure of Example 10 except pyridine was substituted for n-butyl imidazole. The product formed was identified by NMR to contain mainly a cobalt (II) complex and not the alkyl cobalt (III) dioximate of this invention. Comparative Example 11 showed that an imidazole was required to form the alkyl cobalt (III) dioximate of this invention when low pressure hydrogen was used.

What is claimed is:

1. A process for forming an alkyl cobalt (III) dioximate which comprises (1) forming a mixture of a cobalt (II) salt, a dioxime of the formula $R_1$—C(=NOH)—C(=NOH)—$R_2$, an olefinic component, and a Lewis base and (2) treating said mixture with molecular hydrogen under a pressure of 0.7–70 kg/cm$^2$;

wherein the alkyl cobalt (III) dioximate has the following structural formula:

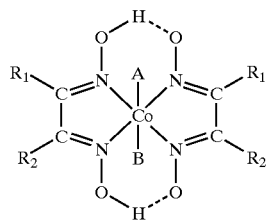

wherein $R_1$, and $R_2$ are individually selected from the group consisting of H, alkyl having at least 2 carbon atoms, substituted alkyl, aryl, substituted aryl, COOR$_5$, CONR$_6$R$_7$, SR$_7$, SO$_2$R$_7$, SO$_2$NR$_5$R$_6$, SOR$_5$, SO$_3$R$_5$, halogen, CCl$_3$, CF$_3$, COR$_5$, CHO, CR$_6$R$_7$OR$_5$, CH(OR$_5$)(OR$_6$), CR$_5$(OR$_6$)(OR$_7$), where $R_5$, $R_6$, and $R_7$ are independently selected from the group consisting of H, alkyl, substituted alkyl, aryl and substituted aryl and A is a substituted alkyl derived from an olefinic component and B is a component of a Lewis base and where the substituents of the substituted alkyl are individually selected from the group consisting of ester, ether, amide, halogen, ketone, hydroxy, aryl, SO$_2$-alkyl, sulfamido, and amino groups and the substituents for the substituted aryl are individually selected from the group consisting of ester, ether, amide, halogen, ketone, hydroxy, alkyl, SO$_2$-alkyl, sulfamido, and amino groups.

2. The process of claim 1 in which the mixture is treated with hydrogen for 0.5 to 5.0 hours at a temperature of −20 to 50° C. and the mixture comprises a cobalt (II) salt, dioxime, olefinic component and Lewis base present in a molar ratio of 1:2:1:1.

3. The process of claim 1 in which the hydrogen used to treat the mixture is under a pressure of 0.7 to 14 kg/cm$^2$ and the Lewis base is selected from the group consiting of imidazole, phosphine and phosphite.

4. The process of claim 3 in which the Lewis base is an imidazole having the structural formula:

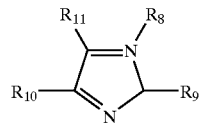

wherein $R_8$, $R_9$, $R_{10}$, and $R_{11}$ are independently selected from the group consisting of H, alkyl, aryl, NR$_5$R$_6$, SR$_7$, SO$_2$R$_7$, SO$_2$N R$_5$R$_6$, SOR$_5$, COR$_5$, CHO, CR$_6$R$_7$OR$_5$, CH(OR$_5$)(OR$_6$), and CR$_5$(OR$_6$)(OR$_7$) and treated with molecular hydrogen under a pressure of 0.7 to 14 kg/cm$^2$; where $R_5$, $R_6$, and $R_7$ are independently selected from the group consisting of H, alkyl, and aryl.

5. The process of claim 3 in which the Lewis base consists of phosphine of the formula P(R$_{14}$)(R$_{15}$)(R$_{16}$), wherein $R_{14}$, $R_{15}$, $R_{16}$ are independently selected from the group consisting of H, alkyl, and aryl.

6. The process of claim 3 in which the Lewis base consists of a phosphite having the formula P(OR$_{17}$)(OR$_{18}$)(OR$_{19}$), where $R_{17}$, $R_{18}$, $R_{19}$ are independently selected from the group consisting of H, alkyl, and aryl.

* * * * *